Figure 1:
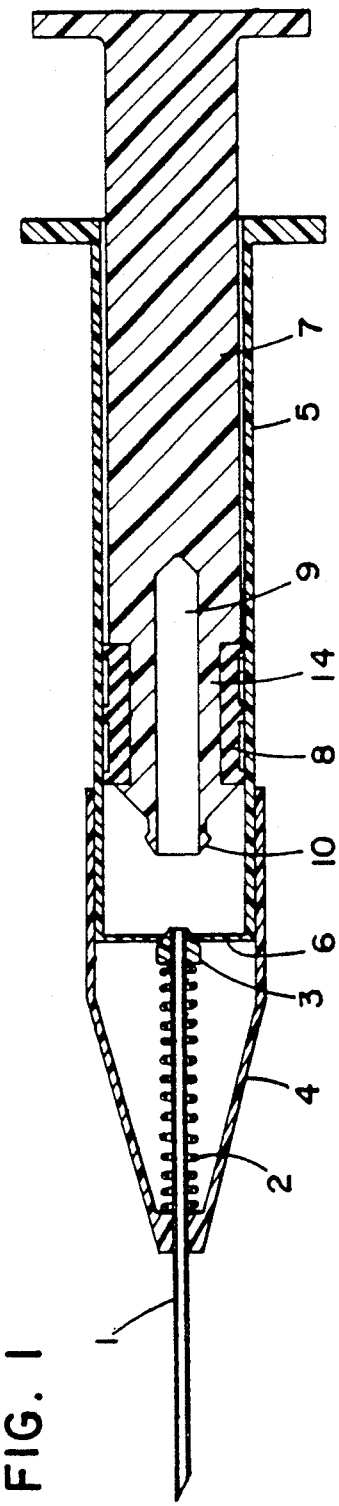

United States Patent [19]

Gaarde

[11] Patent Number: 5,064,419
[45] Date of Patent: Nov. 12, 1991

[54] DISPOSABLE HYPODERMIC SYRINGE

[76] Inventor: Knud W. Gaarde, DK-3050 Humlebaek, Denmark

[21] Appl. No.: 458,637
[22] PCT Filed: Jul. 8, 1988
[86] PCT No.: PCT/DK88/00116
   § 371 Date: Jan. 11, 1990
   § 102(e) Date: Jan. 11, 1990
[87] PCT Pub. No.: WO89/00435
   PCT Pub. Date: Jan. 26, 1989

[30] Foreign Application Priority Data

Jul. 13, 1987 [DK] Denmark .................. 3619/87

[51] Int. Cl.⁵ ................................... A61M 5/00
[52] U.S. Cl. .................... 604/195; 604/198; 604/218; 604/110; 128/919
[58] Field of Search ............ 604/110, 194–198, 604/138, 139, 240, 218

[56] References Cited

U.S. PATENT DOCUMENTS

| | | | |
|---|---|---|---|
| 2,512,882 | 6/1950 | Truesdale | 604/196 X |
| 3,314,428 | 4/1967 | Johnson et al. | 604/192 X |
| 3,890,971 | 6/1975 | Leeson et al. | 604/110 |
| 4,542,749 | 9/1985 | Caselgrandi et al. | 128/752 |
| 4,650,468 | 3/1987 | Jennings, Jr. | |
| 4,747,831 | 5/1988 | Kulli | 604/110 |
| 4,813,940 | 3/1989 | Parry | 604/198 |
| 4,826,484 | 5/1989 | Haber et al. | 604/110 |
| 4,838,863 | 6/1989 | Allard et al. | 604/110 |
| 4,838,869 | 6/1989 | Allard | 604/195 |
| 4,874,382 | 10/1989 | Lindemann et al. | 604/195 |
| 4,900,307 | 2/1990 | Kulli | 604/110 |
| 4,927,414 | 5/1990 | Kulli | 604/110 |
| 4,936,830 | 6/1990 | Verlier | 604/110 |
| 4,955,870 | 9/1990 | Ridderheim et al. | 604/195 |
| 4,966,593 | 10/1990 | Lennox | 604/198 |
| 4,973,316 | 11/1990 | Dysarz | 604/195 |
| 4,978,343 | 12/1990 | Dysarz et al. | 604/195 |
| 4,995,870 | 2/1991 | Baskas | 604/110 |

FOREIGN PATENT DOCUMENTS 0554034  3/1958  Canada .................. 604/139

Primary Examiner—C. Fred Rosenbaum
Assistant Examiner—Mark O. Polutta
Attorney, Agent, or Firm—Merchant & Gould Smith, Edell, Welter & Schmidt

[57] ABSTRACT

Disposable hypodermic syringe comprising a needle (1) which can be retracted and held inside the syringe which moreover comprises a syringe barrel (4, 5) with liquid chamber designed with a piston (14) with a piston rod (7). Opposite the piston (14) the liquid chamber has an entirely or partially yielding end wall (6) with an opening, and the needle (1) is in its end area opposite its point provided with a head (3) which is subjected to the pressure of a spring in the direction toward the yielding wall (6). The piston (14) has a projection with locking means (10) designed to interlock with the opening in the yielding wall (6) when the piston bottoms in that the needle simultaneously snaps into a cavity (9) in the piston through the opening in the yielding wall (6); further usage of the syringe is hereby prevented.

7 Claims, 2 Drawing Sheets

DISPOSABLE HYPODERMIC SYRINGE

The invention relates to a disposable hypodermic syringe of the kind presented.

Today disposable syringes are widely used in hospitals and nursing homes as well as in clinics, dental clinics etc. in order to prevent transmission of infection. Health authorities also strongly advise that drug addicts and the like use disposable syringes because the danger of infection is considered to be extremely large among this group of people. The use of disposable syringes also causes great problems in connection with safe disposal of the large number of used disposable syringes, because disposal and destruction must take place in such a manner that other persons are not exposed to any danger of infection when touching the needles of the disposable syringes.

Disposable syringes should therefore be designed so that they, apart from being used only once, are designed so that the needle after use can be retracted and held inside the syringe.

Such a disposable syringe is known from U.S. Pat. No. 4,650,468 where the needle, following the emptying of the syringe, can be retracted into the syringe barrel and held there. The needle is attached to a piston head which in its position for use is released from the piston and connected with the frontmost end of the syringe barrel. When the piston is pressed down and the syringe is empty, the user will, by twisting the piston rod while the needle protrudes from the syringe, have to release the piston head with the needle from the syringe barrel and then retract the piston rod with the piston head back to an end position in which the piston rod will automatically be locked to the syringe barrel. If the retraction is not effective, the needle can again be moved out of the syringe. Consequently, the design can work according to purpose, but it does in fact comprise at least fifteen single parts which means that the production and assembly costs of the syringe become considerable which is a disadvantage, particularly in connection with a syringe for single use.

The object of the invention is to provide a disposable hypodermic syringe where the retraction of the needle is quick and reliable so that the needle is immediately hidden and the syringe cannot be used again.

This is obtained by designing the disposable syringe according to the invention as presented. Once the piston has reached the bottom, the user will, merely by applying a short further pressure on the piston rod in the same direction as when emptying the syringe, make the needle snap all the way back into the syringe. Consequently, no particularly directions are required as to how to render the syringe harmless since this is done the minute the syringe is emptied completely.

By designing the hypodermic syringe according to the invention as presented in the specification and claims, the piston will become locked in its bottom position so that it cannot be retracted if for instance somebody tries to use the syringe again. This is a double safeguard against repeated use, and even during attempts at using the syringe again, the needle will remain inside the syringe barrel so that no danger of infection occurs.

The hypodermic syringe according to the invention can be designed as presented in the claims and specification in that the piston with piston rod and the forwardly pointed cone with projections can be designed as a unit by injection moulding in order that the embodiment does not require further individual parts. Besides, the hypodermic syringe according to the invention only comprises a specific number of individual parts.

By designing the hypodermic syringe according to the invention as presented in the claims and specification, the spring effect is obtained in a simple, reliable and very inexpensive manner since ordinary helical springs are standard equipment which are available in large quantities at very low prices.

By designing the hypodermic syringe according to the invention as presented in the claims and specifications, an embodiment is obtained where the cavity in the piston is shut off from the liquid chamber proper and the air present in this.

Figure 2:
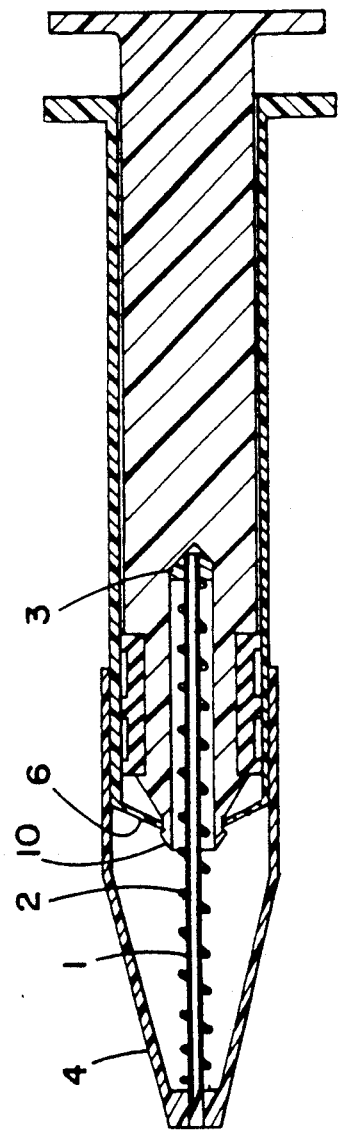
Figure 3:
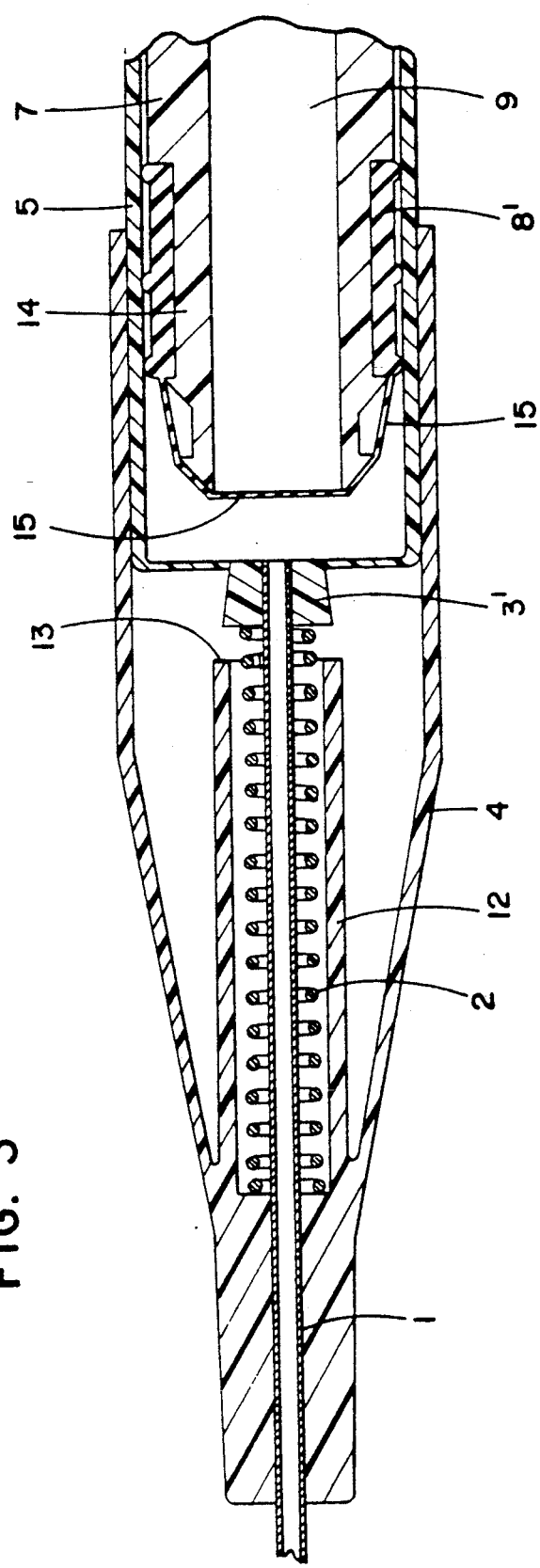

In the following the invention will be described in closer detail with reference to the drawing, in which FIG. 1 shows a section through a hypodermic syringe according to a first embodiment of the invention and prior to usage, FIG. 2 shows a section through the same hypodermic syringe, but after usage, and FIG. 3 shows a section on a larger scale through the needle part of a hypodermic syringe according to a second embodiment.

The hypodermic syringe on FIGS. 1 and 2 comprises a cylindrical barrel 5 and a spring retainer 4 attached to said barrel in that the barrel 5 and the spring retainer 4 are joined in a generally known manner, e.g. by glueing or by ultrasonic welding.

A piston 14 with piston rod 7 is arranged in the barrel 5 designed in one piece as a unit. A piston packing 8 is attached to the piston in a circularly extending groove in order to seal the liquid chamber situated below the piston, and an oblong cavity 9 is provided centrally in the piston the function of which cavity will be described later.

The needle 1 of the hypodermic syringe is situated in the spring retainer 4, cf. FIG. 1 and surrounded by a pre-set spring 2 which by a suitable pressure, e.g. 3–400 g, forces the needle towards the bottom 6 of the syringe barrel. The needle 1 and the spring 2 are controlled by the spring retainer 4. A head 3 is moulded onto the needle 1, said head for instance being tapered, as illustrated and being slightly larger than a hole in the end wall 6 of the syringe barrel 5, said wall being designed as a comparatively thin and yielding wall. Due to the spring pressure from the spring 2 the head 3 is sealed toward the rim of the opening in the yielding end wall 6.

Around the opening onto the cavity 9 the piston 14 has a protruding part which is designed for instance as a cone with projections 10, as illustrated.

When the piston rod 7 and the piston 14 are being pressed down, as shown in FIG. 2, the cone at the end of the piston will push forward the bottom 6 of the syringe barrel up to describe an arc which causes the diameter of the hole in the bottom to increase slightly, and the needle spring 2 can now push up the needle 1 and the needle head 3 into the cavity in the piston which is done with a slight click so that the user will always know when the syringe is empty and cannot be used again.

The thin bottom in the syringe barrel is simultaneously moved across the projections 10 of the piston, said projections being designed so that for instance a circularly extending groove is provided behind the projections in order that the piston and piston rod can no longer be withdrawn. It is clearly seen from FIG. 2 that the needle hereby becomes completely hidden in the syringe barrel in that it has been pushed up into the cavity 9 in the piston by the spring 2, and that the piston is locked.

The embodiment shown in FIGS. 1 and 2 of the drawing should be taken as an illustrative embodiment for explanation of the mode of operation of the hypodermic syringe. It will be obvious to anyone skilled in the art that the details, particularly concerning the embodiment of the piston 14 with the cavity 9 and the lock projections 10 and the embodiment of the yielding end wall 6 and the sealing head 3 of the needle 1, can be designed in many other ways than the one which is shown and described.

FIG. 3 shows an embodiment where the packing 8' is designed in a special way, viz. with a thin membrane 15 surrounding the tapered end of the piston 14 and thus completely seals off the opening to the cavity 9. Moreover, the head 3' on the needle is shown in an embodiment being slightly different to the one according to FIGS. 1 and 2. Around the spring 2 a cylindrical collar 12 is arranged whose upper rim 13 is situated at a comparatively short distance to the head 3' of the needle. All other parts are identical to those shown in FIGS. 1 and 2 and have therefore been given the same reference numbers.

When the piston 14 bottoms by usage of the hypodermic syringe shown in FIG. 3, the head 3' of the needle will rest against the face 13 and can thereby puncture or destroy the membrane 15 so that the needle 1 is displaced up into the cavity 9 in the piston which is locked, quite similarly to the manner described in connection with FIG. 2 of the drawing. Any connection between the liquid chamber and the cavity 9 is hereby prevented until the hypodermic syringe is empty.

I claim:

1. A disposable hypodermic syringe with a needle which can be retracted and held inside the syringe, comprising:
   a hollow syringe barrel with two ends, containing a piston with an attached piston rod inserted in one end, said piston rod extending out of said end and a spring retainer attached to said syringe barrel at the other end;
   a needle having a point at one end and a head attached to the other, said point extending out of said spring retainer;
   a liquid chamber within said syringe barrel which has a yielding end wall opposite said piston, with an opening in said yielding end wall that is smaller then said needle head;
   a spring within said spring retainer for maintaining pressure between said needle head and said opening in said yielding end wall, wherein the spring force is sufficient to maintain a liquid tight seal between said needle head and said opening of said yielding end wall; and
   a cavity in said piston opposite said opening in said yielding end wall which receives said needle when the piston is pushed sufficiently forward to allow the head of the needle to pass through the opening in said yielding end wall.

2. A disposable hypodermic syringe according to claim 1, wherein said piston has projections located proximate to said cavity, pointing in the direction of said yielding end wall, said projections comprising:
   means to widen the opening in said end wall when said piston is pushed forward; and
   means to interlock said end wall with said projections on said piston.

3. A disposable hypodermic syringe according to claim 2, wherein said projections on said piston are substantially cone shaped to allow passage through said widened opening in said end wall in the direction of travel.

4. A disposable hypodermic syringe according to claim 1, wherein said spring pressure is established by means of a pre-set helical spring situate around said needle and resting on said needle head.

5. A disposable hypodermic syringe according to claim 1, wherein piston packing is attached to said piston for sealing said liquid chamber and for covering said piston cavity.

6. A disposable hypodermic syringe according to claim 5, wherein said piston packing contains a membrane to cover said piston cavity.

7. A disposable hypodermic syringe according to claim 6, wherein a cylindrical collar located in said spring retainer supports said needle head against pressure from said advancing piston.

* * * * *